United States Patent [19]

Duffett

[11] Plant 5,163

[45] Dec. 20, 1983

[54] CHRYSANTHEMUM PLANT

[75] Inventor: William E. Duffett, Salinas, Calif.

[73] Assignee: Yoder Brothers, Inc., Barberton, Ohio

[21] Appl. No.: 343,259

[22] Filed: Jan. 27, 1982

[51] Int. Cl.[3] ..... A01H 5/00
[52] U.S. Cl. ..... Plt./76
[58] Field of Search ..... Plt./76, 79, 82

*Primary Examiner*—Robert E. Bagwill
*Attorney, Agent, or Firm*—Schwartz, Jeffery, Schwaab, Mack, Blumenthal & Koch

[57] ABSTRACT

A chrysanthemum plant known by the cultivar name Sequoia and particularly characterized as to uniqueness by the combined characteristics of flat capitulum form, decorative capitulum type; red bronze ray floret color; diameter across face of capitulum ranging from 100 to 125 mm. at maturity; uniform 10 week photoperiodic flowering response to short days; medium plant height when grown as a pinched, disbudded pot; spreading branching pattern, and having a photosynthetic efficiency sufficient to produce strong plants under low, winter light regimes with 14 to 16 hour continuous dark periods.

3 Drawing Figures

1

The present invention comprises a new and distinct cultivar of *Chrysanthemum morifolium,* Ramat., hereinafter referred to by the cultivar name Sequoia.

Sequoia is a product of a planned breeding program which had the objective of creating new chrysanthemum cultivars for low light, pinched pot mum programs having decorative capitulum type, red bronze ray floret color, 10 week flowering response and having the ability to produce commercially acceptable quality in late fall, winter and early spring programs. Such traits in combination were not present in previously available commercial cultivars.

Sequoia was originated from x-radiation in a controlled mutation induction program in Salinas, Calif. in 1979. The female parent of the irradiated seedling was Royal Purple, a non-patented commercial cultivar of unknown parentage. Royal Purple is a flat, dark pink decorative disbud pot mum. The male parent of the irradiated seedling was Mandalay, a non-patented commercial cultivar originated from a cross between Woking Scarlet and Mayford Crimson. Mandalay is a flat, bronze decorative disbud pot mum. The x-ray dose level utilized was 900 rads.

Sequoia was discovered and selected as one flowering plant within the irradiated population by William E. Duffett on May 21, 1979 in a controlled environment in Salinas, Calif.

The first act of asexual reproduction of Sequoia was accomplished when vegetative cuttings were taken from the initial selection in Aug. 1979 in a controlled environment in Salinas, Calif. by a technician working under formulations estabished and supervised by William E. Duffett. Horticultural examination of selected units initiated Oct., 1979 has demonstrated that the combination of characteristics as herein disclosed for Sequoia are firmly fixed and are retained through successive generations of asexual reproduction.

Sequoia has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

2

The following traits have been repeatedly observed and are determined to be basic characteristics of Sequoia which in combination distinguish this chrysanthemum as a new and distinct cultivar:

(1) flat capitulum form;

(2) decorative capitulum type;

(3) bronze red ray floret color;

(4) diameter across face of capitulum ranging from 100 to 125 mm. at maturity;

(5) uniform 10 week photoperiodic flowering response to short days;

(6) medium plant height (requiring 1–2 long day weeks prior to pinch and short days, and one application 2500 ppm B-9 SP 14 to 21 days after the beginning of short days to attain a flowered plant height of 30 to 40 cm.);

(7) spreading branching pattern; and (8) photosynthetic efficiency sufficient to produce strong plants under low, winter light regimes with 14 to 16 hour continuous dark periods.

The accompanying photographic drawings depict typical foliage and inflorescence characteristics of Sequoia. Sheet 1 is a color photograph of a plant of Sequoia grown as a pinched disbud, with colors being as accurate as possible with renditions of this type. Sheet 2 is a black and white photograph of three views of the inflorescence of Sequoia. Sheet 3 shows the foliage of Sequoia in three stages of growth.

Of the many commercial cultivars known to the present inventors, the most similar in comparison to Sequoia is Mandarin. Reference is made to attached Chart A which compares certain characteristics of Sequoia to those same characteristics of Mandarin.

In comparison to Mandarin, Sequoia has a darker red bronze flower color, higher ray petal count and superior photosynthetic efficiency resulting in stronger plants under low light regimes. Response is 10 weeks versus 9 weeks. The capitulum form, shape and branching pattern are similar to those same characteristics of Mandarin.

In the following description, color references are made to The Royal Horticultural Society Colour Chart. The color values were determined between 10:00 and 10:15 A.M. on Oct. 21, 1981 under 150 foot-candle light intensity at Salinas, Calif.

Classification:

*Bontanical.*—*Chrysanthemum morifolium,* Ramat., cv Sequoia.

*Commercial.*—Pinched Disbudded Pot Mum.

1. Inflorescence:

A. *Capitulum.*—Form: Flat. Type: Decorative. Diameter across face: 100 to 125 mm.

B. *Corolla of ray florets.*—Color (general tonality from a distance of three meters): Red bronze. Color (abaxial): Immature approximately 45B, with very rapid oxidation to 171-A to 171-C, with base of floret showing 163-B, 171-A to 171-C with base of 163-B. Color (adaxial): 11-C darkening to 20-C with fine streaks of 173-B. Persistence: Resists shatter.

C. *Corolla of disc florets.*—Color (mature): 14-A. Color (immature): 4-B. Scant: Few to absent.

D. *Reproductive organs.*—Androecium: Present disc florets only; scant pollen. Gynoecium: Present both ray and disc florets.

II. Plant:

A. *General appearance.*—Height: Medium; 30 to 40 cm. given 2 long day weeks before pinch and lights out, and 1–2 applications 2500 B-9 SP after the beginning of short days. Branching pattern: Spreading.

B. *Foliage.*—Color (abaxial): 137-A. Color (adaxial): 138-B to 138-C. Shape: Deeply lobed and moderately serrated.

CHART A

COMPARISON OF SEQUOIA AND MANDARIN

| CULTIVAR | RAY FLORET COLOR | CAPITULUM FORM AND TYPE | BRANCHING PATTERN |
|---|---|---|---|

CHART A-continued

COMPARISON OF SEQUOIA AND MANDARIN

| | | | |
|---|---|---|---|
| Sequoia | Red Bronze | Flat Decorative under low light Few to no disc Florets | Spreading |
| Mandarin | Dark Bronze | Flat Decorative under low light disc florets are abundant | Spreading |

| CULTIVAR | DIAMETER ACROSS FACE OF CAPITULUM | PLANT HEIGHT | FLOWERING RESPONSE PERIOD |
|---|---|---|---|
| Sequoia | 100 to 125 mm. | 30 to 40 cm. | 10 week Requires a minimum 14 hour dark period. |
| Mandarin | 75 to 100 mm. | 20 to 30 cm. | 9 week Develops in a minimum 13 hour dark period. |

COMPARISONS MADE OF PLANTS GROWN AS PINCHED AND DISBUDDED POT MUMS IN SALINAS, CALIFORNIA.

I claim:

1. A new and distinct cultivar of *Chrysanthemum morifolium,* Ramat., plant known by the cultivar name of Sequoia, as described and illustrated, and particularly characterized as to uniqueness by the combined characteristics of flat capitulum form; decorative capitulum type; red bronze ray floret color; diameter across face of capitulum ranging from 100 to 125 mm. at maturity; uniform 10 week flowering response; medium plant height; spreading branching pattern, and by its photosynthetic efficiency, producing strong plants under low winter light regimes with 14 to 16 hour continuous dark periods.

* * * * *

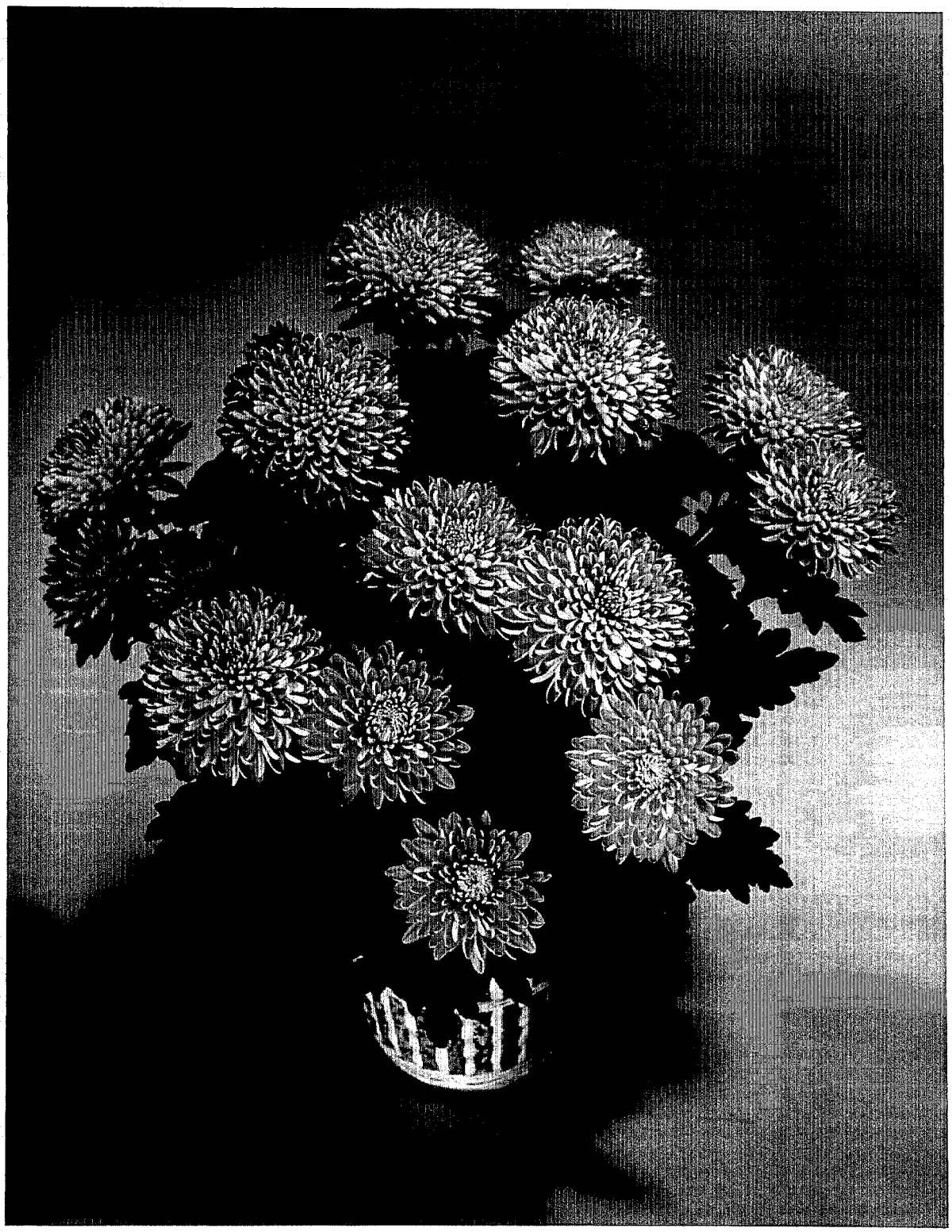

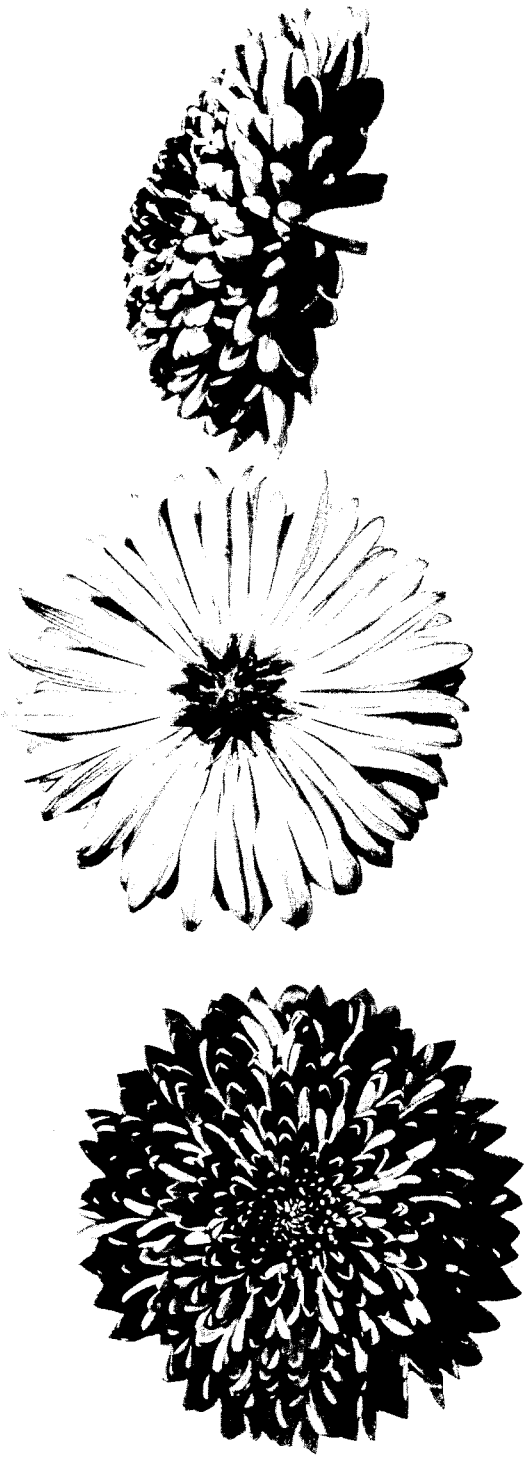

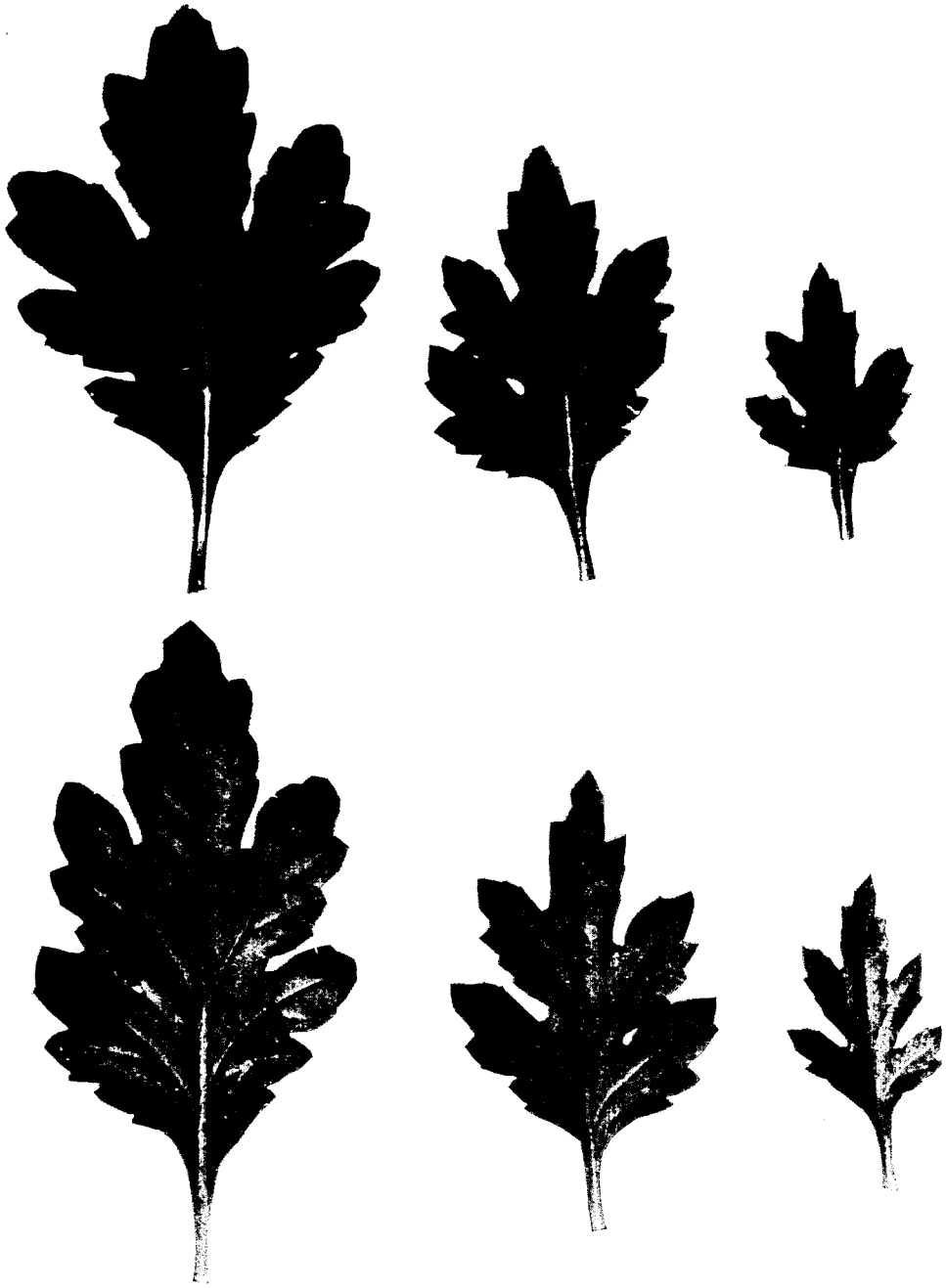

UNITED STATES PATENT AND TRADEMARK OFFICE

CERTIFICATE OF CORRECTION

PATENT NO. : PP 5163

DATED : December 20, 1983

INVENTOR(S) : WILLIAM E. DUFFETT

It is certified that error appears in the above—identified patent and that said Letters Patent is hereby corrected as shown below:

--In lines 14 and 15, column 3, delete the following: "171-A to 171-C with base of 163-B". Change the comma after "163-B," in line 14 to a period.

Signed and Sealed this

*Seventeenth* Day of *April 1984*

[SEAL]

*Attest:*

GERALD J. MOSSINGHOFF

*Attesting Officer*

*Commissioner of Patents and Trademarks*